US012808814B2

(12) United States Patent
Doerries et al.

(10) Patent No.: US 12,808,814 B2
(45) Date of Patent: Nov. 24, 2026

(54) MOTION BASED DYNAMIC TENSIOMETER FOR DETECTING THE PRESENCE OF SURFACTANTS

(71) Applicant: ECOLAB USA INC., Saint Paul, MN (US)

(72) Inventors: Stephan Doerries, Düsseldorf (DE); Thomas Wershofen, Monchengladbach (DE)

(73) Assignee: ECOLAB USA INC., Saint Paul, MN (US)

( * ) Notice: Subject to any disclaimer, the term of this patent is extended or adjusted under 35 U.S.C. 154(b) by 271 days.

(21) Appl. No.: 18/405,496

(22) Filed: Jan. 5, 2024

(65) Prior Publication Data

US 2024/0328959 A1 Oct. 3, 2024

Related U.S. Application Data

(60) Provisional application No. 63/492,407, filed on Mar. 27, 2023.

(51) Int. Cl.
*G01N 21/88* (2006.01)
*G01N 21/85* (2006.01)
(Continued)

(52) U.S. Cl.
CPC ......... *G01N 21/8851* (2013.01); *G01N 21/85* (2013.01); *G01N 33/18* (2013.01); *G06T 9/00* (2013.01); *G01N 2021/8887* (2013.01)

(58) Field of Classification Search
CPC .... G01N 21/8851; G01N 21/85; G01N 33/18; G01N 2021/8887; G01N 13/02; G06T 9/00
See application file for complete search history.

(56) References Cited

U.S. PATENT DOCUMENTS

| | | | | |
|---|---|---|---|---|
| 10,908,074 | B1 * | 2/2021 | Menkara ................ | G01N 21/85 |
| 2004/0253737 | A1 | 12/2004 | Haberland et al. | |

(Continued)

FOREIGN PATENT DOCUMENTS

| | | | |
|---|---|---|---|
| CN | 111189789 | A | 5/2020 |
| JP | 2003075348 | A | 3/2003 |
| WO | 2010018285 | A1 | 2/2010 |

OTHER PUBLICATIONS

Karasawa et al, ("Motion modes of two self-propelled camphor boats on the surface of a surfactant-containing solution", Journal of Colloid and Interface Science 511 (2018) 184-192) (Year: 2018).*

(Continued)

*Primary Examiner* — Amara Abdi
(74) *Attorney, Agent, or Firm* — McKee, Voorhees & Sease, PLC

(57) ABSTRACT

A device that detects the presence of surfactant residues utilizes a motion-based camphor test to detect surfactant(s) and surface-active molecules. The device, also referred to as a camphor-based dynamic tensiometer, can be used to detect desirable and/or undesirable surfactant(s). For example, surfactants used for membrane cleaning, as surface active ingredients, need to be rinse out of surfaces. Especially for porous membranes the rinsing of the Permeate side is water-intensive, since the huge membrane area of the porous structure. Thus, a camphor-based dynamic tensiometer can be automated to determine end of rinse in systems that utilize CIP chemistries containing surfactant(s). Proper rinse of CIP chemistry(ies) is key while removing the cleaning chemistry and balancing on the other hand water spent for the rinse, as membranes are difficult to rinse due to the porosity of the membrane towards the permeate site and the big inner surface of the porous structure.

15 Claims, 10 Drawing Sheets

(51) Int. Cl.
*G01N 33/18* (2006.01)
*G06T 9/00* (2006.01)

(56) References Cited

U.S. PATENT DOCUMENTS

| | | | |
|---|---|---|---|
| 2005/0126599 | A1 | 6/2005 | Labib et al. |
| 2007/0171298 | A1* | 7/2007 | Kurane .................. H04N 23/73 348/E5.037 |
| 2010/0009430 | A1* | 1/2010 | Wan .................. B01L 3/502746 422/68.1 |
| 2011/0272598 | A1 | 11/2011 | Okawa et al. |
| 2014/0274857 | A1 | 9/2014 | Schacht et al. |
| 2015/0226683 | A1* | 8/2015 | Feldman ................ G01N 22/04 324/639 |
| 2015/0293094 | A1 | 10/2015 | Ladisch et al. |
| 2015/0343386 | A1* | 12/2015 | Labib ......................... A61L 2/00 |
| 2016/0033383 | A1* | 2/2016 | Grinstaff ................ G01N 13/02 73/64.48 |
| 2019/0099720 | A1 | 4/2019 | Schacht et al. |
| 2019/0225678 | A1* | 7/2019 | Muellershausen ........ A61P 7/04 |
| 2023/0047115 | A1* | 2/2023 | Cagnazzo ................. G06T 3/40 |
| 2023/0190121 | A1* | 6/2023 | Watanabe ............ A61B 5/6817 600/301 |
| 2023/0283976 | A1* | 9/2023 | Ninan ...................... H04S 7/304 381/303 |
| 2024/0036029 | A1* | 2/2024 | Das .................. G01N 33/48792 |

OTHER PUBLICATIONS

EX-100 Specifications, Casio, 2022, 6 pages.
Fei W, Gu Y, Bishop KJ. Active colloidal particles at fluid-fluid interfaces. Current opinion in colloid & interface science. Nov. 1, 2017;32:57-68.
International Search Report and Written Opinion in PCT/US2024/010444, mailed Jun. 4, 2024, 23 pages.
Karasawa Y, Nomoto T, Chiari L, Toyota T, Fujinami M. Motion modes of two self-propelled camphor boats on the surface of a surfactant-containing solution. Journal of colloid and interface science. Feb. 1, 2018;511:184-92.
Nakata S, Iguchi Y, Ose S, Kuboyama M, Ishii T, Yoshikawa K. Self-rotation of a camphor scraping on water: new insight into the old problem. Langmuir. Aug. 6, 1997;13(16):4454-8.
Paven M, Mayama H, Sekido T, Butt HJ, Nakamura Y, Fujii S. Light-driven delivery and release of materials using liquid marbles. Advanced Functional Materials. May 2016;26(19):3199-206.
Drop Volume Tensiometer DVT50, Krüss Technical Information, 2009, 4 pages.
Nakata S, Murakami M. Self-motion of a camphor disk on an aqueous phase depending on the alkyl chain length of sulfate surfactants. Langmuir. Feb. 16, 2010;26(4):2414-7.
Nakata S, Nagayama M. Chapter 1: Theoretical and experimental design of self-propelled objects based on nonlinearity, in Self-organized Motion: Physicochemical Design based on Nonlinear Dynamics. 2018;1-34.
Suematsu NJ, Sasaki T, Nakata S, Kitahata H. Quantitative estimation of the parameters for self-motion driven by difference in surface tension. Langmuir. Jul. 15, 2014;30(27):8101-8.
Xu Y, Takayama N, Er H, Nakata S. Oscillatory motion of a camphor object on a surfactant solution. The Journal of Physical Chemistry B. Jan. 28, 2021;125(6):1674-9.
YouTube video entitled: "Camphor Dances on water (surface tension experiment)," uploaded May 14, 2018 by user "Video Eppo" [retrieved Oct. 31, 2022]. Retrieved from the Internet: <URL:https://www.youtube.com/watch?v=AjiRDjebSts>, 1 page.

* cited by examiner

300

| Classification | Observation | Characterized by: |
|---|---|---|
| 0 | No Movement of Crystals | High Surfactant Load |
| 1 | Low Movement of Crystals | Crystals Stop Dancing After Short Period (e.g., <2s) |
| 2 | Medium Dancing | Crystals Stop Dancing After Long Period (e.g., ~10s) |
| 3 | Intensive Dancing | Crystals Do Not Stop Dancing After Long Period (e.g., <10s) |

FIG. 9

MOTION BASED DYNAMIC TENSIOMETER FOR DETECTING THE PRESENCE OF SURFACTANTS

CROSS REFERENCE TO RELATED APPLICATIONS

This application claims priority under 35 U.S.C. § 119 to U.S. provisional patent application Ser. No. 63/492,407, filed Mar. 27, 2023. The provisional patent application is herein incorporated by reference in its entirety, including without limitation, the specification, claims, and abstract, as well as any figures, tables, appendices, or drawings thereof.

TECHNICAL FIELD

The present disclosure relates generally to methods for detecting the presence of surfactants in rinse water that has been used to remove clean-in-place (CIP) chemistries from the surface(s) of industrial equipment. Depending on the detected level of surfactants on said surface(s), the present disclosure further identifies how to effectively employ cleaning compositions and/or clean-in-place (CIP) chemistries to purge solutions of said surfactants.

More particularly, but not exclusively, the present disclosure relates to an automated membrane end of rinse surfactant residue detection device utilizing camphor testing, imaging technology, and automated means for cleaning fluidic systems of surfactants.

BACKGROUND

The background description provided herein gives context for the present disclosure. Work of the presently named inventors, as well as aspects of the description that may not otherwise qualify as prior art at the time of filing, are neither expressly nor impliedly admitted as prior art.

Surfactants are critical for cleaning membrane equipment to clean soils like fat and proteins in food and beverage industries. Membrane technology surfactants, as surface active ingredients, interact with the porous inner surface of the membrane towards the permeate side. As a result, rinse times to remove the surfactants can be quite lengthy. This results in an inefficient consumption of water during rinse.

Incomplete removal of membrane fouling impacts membrane production performance. Furthermore, the incomplete removal of membrane fouling proves to be a significant factor in overall membrane health. Surfactants are needed to remove these foulants.

Thus, a need in the art exists for accurately identifying when dairy membrane cleaning composition(s) used in rinse water are effective to purge solutions of surfactant(s).

At present, others in the art determine end of rinse based on a time spent rinsing or by using conductivity to rinse to a level similar to the rinse water used. Manually setting a time of rinse is prone to human error and high safety margins need to be included, wasting water. Too much time spent rinsing results in efficiencies and increases the costs of cleaning. Too little time spent rinsing results in not removing all CIP agents, and foulants present in the CIP solution. Moreover, as many of these types of macromolecules and surfactants are not sensitive to conductivity, present method(s) that automize end of rinse detection devices based on conduction are not accurate. Conductivity based methods to determine end of rinse are thus not sufficient to address the need to purge solutions of surfactant(s).

In view of the foregoing problems in the art, there exists a further need in the art for a device and related method(s) that more easily and accurately determines the presence of surface-active ingredients at a parts-per-million (ppm) level, so that optimal efficiency in cleaning process(es) can be achieved.

SUMMARY

The following objects, features, advantages, aspects, and/or embodiments, are not exhaustive and do not limit the overall disclosure. No single embodiment need provide each and every object, feature, or advantage. Any of the objects, features, advantages, aspects, and/or embodiments disclosed herein can be integrated with one another, either in full or in part.

It is a primary object, feature, and/or advantage of the present disclosure to improve on or overcome the deficiencies in the art.

It is a further object, feature, and/or advantage of the present disclosure to utilize camphor(s), which can "dance" on the surface of a fluid depending on the surface tension of the fluid to detect the presence of surfactants that are known to affect said surface tension.

It is still a further object, feature, and/or advantage of the present disclosure to quantify the static surface tension of rinse water that may contain surfactants. An operator viewing an imaging system can manually access movement of crystals for a period of time. Depending on how much movement is detected, a classification can then be given. For example, a 0 can represent no movement of crystal (high surfactant load); a 1 can represent low movement of crystals with stop after short period; a 2 can represent medium dancing, such as when it takes ten seconds for a crystal to stop dancing; and a 3 can represent intensive dancing of the camphor crystal. Automated measurements can also be sensed. For example, objective parameters such as the rotational speed of the crystals can be sensed using the imaging technology.

It is still a further object, feature, and/or advantage of the present disclosure to embody the ability to use camphor crystals and other mechanisms that induce motion in fluidic bodies based on a difference in surface tension to measure same in a device. Such devices can therefore be considered motion based dynamic tensiometers. And more particularly, where camphor crystals are the driving mechanism for the surface tension of a fluid, such devices are camphor-based, imaging technology-based, dynamic tensiometers.

It is a further object, feature, and/or advantage of the present disclosure to minimize the total time it takes to make a measure with such a device. For example, the maximum time it takes to measure the static surface tension in the fluid can be as little as ten to fifteen seconds (10 sec.-15 sec.).

It is still yet a further object, feature, and/or advantage of the present disclosure to routinely clean and deeply clean fluidic bodies. For example, the above SOPs can use the cleaning compositions described herein to clean existing plumbing systems "in place". Such cleaning methods are known as clean-in-place ("CIP") methods.

It is still yet a further object, feature, and/or advantage of the present disclosure to improve the efficacy of using dairy membrane cleaning compositions through more precise identification of when cleaning has been accomplished and rinse has ended.

It is still yet a further object, feature, and/or advantage of the present disclosure to optimize rinse time, so as to lead to water savings while properly rinsing out CIP residues.

The dynamic tensiometer disclosed herein can be used in a wide variety of applications. For example, the methods for detecting the presence of surfactants for CIP applications, in the food and beverage industry, Biotechnology, Life Science, Pharmaceutical industry and in the cleaning commercial sector generally. Further applications include institutional (including FSR, HHC, & Professional Products), health care, quick serve restaurants, pest elimination, textile care/laundry (e.g., washing machine rinse optimization), water paper, mining, sensors, energy services, and consumer markets.

It is still yet a further object, feature, and/or advantage of the present disclosure to positively impact key performance indicators (KPIs) that are integral to sustaining continued customer satisfaction. Such KPIs can include, but are not limited to including, the time it takes to maintain equipment cleaned with CIP chemistries; the expense of cleaning said equipment; and/or the quality of food and beverages produced with equipment cleaned with CIP chemistries.

It is preferred the camphor-based dynamic tensiometer be safe, cost effective, and durable. For example, the quantification should be reliable enough to definitively determine whether surfactant and CIP chemistry residues have been eliminated from a surface. The camphor-based tensiometer should also be adapted to resist excessive heat, static buildup, corrosion, and/or mechanical failures (e.g., cracking, crumbling, shearing, creeping) due to excessive impacts and/or prolonged exposure to tensile and/or compressive forces acting on the dynamic-based tensiometer so that the dynamic based tensiometer has the longest possible usable lifetime.

It is a further object, feature, and/or advantage of the present disclosure to beneficially remove fouling and clean filtration membranes such as microfiltration, ultrafiltration, nanofiltration, or reverse osmosis membranes, typically utilized in dairy production.

Beside surfactants other molecules could be surface active like foulants such as fats, fatty acids, proteins etc. The device could be used in combination with surfactants during membrane cleaning steps to optimize the total CIP procedure and in all rinse phases. Also, determination of surfactant concentration is possible.

Methods can be practiced which facilitate use, manufacture, assembly, maintenance, and repair of dynamic tensiometers which accomplish some or all of the previously stated objectives.

The dynamic tensiometer can be incorporated into automated systems which clean equipment used to produce food and beverages and accomplish some or all of the previously stated objectives.

According to some aspects of the present disclosure, a process for evaluating characteristics of a fluidic body comprises sampling a portion of the fluidic body; applying camphor crystals to the sampled portion of the fluidic body; monitoring movement of the camphor crystals in the sampled portion of the fluidic body with imaging technology; and determining whether the camphor crystals are dancing in the sampled portion of the fluidic body.

According to some additional aspects of the present disclosure, the determination of whether the camphor crystals are dancing in the sampled portion of the fluidic body further comprises determining a degree to which the camphor crystals are dancing in the sampled portion of the fluidic body.

According to some additional aspects of the present disclosure, the fluidic body is rinse water that has been used to clean dairy membranes. Furthermore, an amount of surfactants in the rinse water can be quantified based upon the determination of whether the camphor crystals are dancing in the sampled portion of the fluidic body.

According to some additional aspects of the present disclosure, the sampled portion of the fluidic body is sampled within a bypass section of piping.

According to some additional aspects of the present disclosure, wherein the sampled portion of the fluidic body is sampled within a sample box. Optionally, one or more valves can allow flow into and/or out of the sample box.

According to some additional aspects of the present disclosure, the application of camphor crystals to the sampled rinse water occurs in a modulated release.

According to some additional aspects of the present disclosure, a weight, volume, and/or amount of the camphor crystals released in the modulated release is manually set by the user.

According to some additional aspects of the present disclosure, a weight, volume, and/or amount of the camphor crystals released in the modulated release is automatically determined by a controller additionally including the use of the camera checking the release in the sample box.

According to some additional aspects of the present disclosure, the process further comprises crushing and transporting the camphor crystal(s) to the sample box. Optionally, the crushing and transporting are accomplished with an auger.

According to some additional aspects of the present disclosure, the camphor crystals are transported from a camphor supply to a surface of the sampled portion of the fluidic body.

According to some additional aspects of the present disclosure, a load sensor alerts a user when an amount of the camphor crystals in the camphor supply is low.

According to some additional aspects of the present disclosure, the process further comprises analyzing whether there is a presence of surfactants in the sampled fluidic body. The analyzing can comprise evaluating a sequence of images captured in succession at a set time interval. As an example, the set time interval can be approximately 0.10 seconds. Optionally, the analyzing can be carried out by artificial intelligence (AI), the imaging technology (e.g., a video camera), and/or a customer programmable logic controller.

According to some additional aspects of the present disclosure, the process further comprises compressing the sequence of images.

According to some additional aspects of the present disclosure, the process further comprises maintaining a connection to a local network with the imaging technology.

According to some additional aspects of the present disclosure, the process further comprises connecting the video, internet protocol (IP) camera to the Internet, a controller, and/or a close-loop controller.

According to some additional aspects of the present disclosure, the process further comprises storing recorded images and/or videos on non-volatile computer memory. The non-volatile computer memory can comprise flash memory and/or a hard disk drive.

According to some additional aspects of the present disclosure, the imaging technology further comprises an IR module for detecting motion of objects in the sampled portion of the fluidic body with imaging technology.

According to some additional aspects of the present disclosure, the process further comprises utilizing a high contrast background to facilitate the determination of whether the camphor crystals are dancing in the sampled portion of the fluidic body.

According to some additional aspects of the present disclosure, the process further comprises draining the sampled portion of the fluidic body through a drain.

According to some other aspects of the present disclosure, a process for evaluating characteristics of a fluidic body comprises transporting a mechanism from a supply to a surface of the fluidic body; activating the mechanism by utilizing a difference in surface tension in a first area of a fluidic body and a second area of the fluidic body proximate the first area; monitoring rotational and/or oscillatory movement of the mechanism with imaging technology; and classifying and/or quantifying the rotational and/or oscillatory movement of the mechanism with imaging technology and a controller.

According to some additional aspects of the present disclosure, the mechanism can comprise camphor crystals; an oscillatory chemical reaction, such as Fe(phen)32+ (ferroin) transforming into Fe(phen)33+ (ferrin) alternately; or self-propelled droplets, such as a mercury droplet or a butyl salicylate (BS) droplet.

According to some additional aspects of the present disclosure, the controller controls and actuates one or more valves which allow for flow of a fluid to move into and out of a container that samples the fluidic body.

According to some additional aspects of the present disclosure, the classification is based on a table having guidelines for evaluating the rotational and/or oscillatory movement of the mechanism.

According to some additional aspects of the present disclosure, the process further comprises utilizing infrared technology or other technology to initially detect the rotational and/or oscillatory movement of the mechanism.

According to some other aspects of the present disclosure, a camphor-based dynamic tensiometer comprises a container; a camphor supply; a dispensing mechanism for transporting and crushing camphor from the camphor supply to the container; an IP camera; and a controller for analyzing movement of the camphor when applied at a surface of a fluidic body.

According to some additional aspects of the present disclosure, the container is a bypass that pulls rinse water from piping.

According to some additional aspects of the present disclosure, the camphor supply comprises a load sensor.

According to some additional aspects of the present disclosure, the camphor is a natural camphor.

According to some additional aspects of the present disclosure, the camphor is a synthetic camphor.

According to some additional aspects of the present disclosure, wherein the IP camera comprises the controller and the controller comprises a central processing unit and a graphics processing unit.

According to some additional aspects of the present disclosure, wherein the IP camera relays images and videos to the controller and the controller comprises a customer programmable logic controller.

According to some additional aspects of the present disclosure, the dispensing mechanism comprises an auger.

According to some additional aspects of the present disclosure, the camphor-based dynamic tensiometer further comprises one or more valves that control fluid flow into and/or out of the container.

According to some additional aspects of the present disclosure, the one or more valves are actuated by the controller.

According to some other aspects of the present disclosure, a method of evaluating cleaning and rinsing of a membrane with a surfactant composition comprises initially cleaning the membrane with the surfactant composition; monitoring for a presence of an undesirable polymeric macromolecules in a solution that is passed through the membrane after the initial cleaning by applying camphor to said solution; identifying a presence of undesirable polymeric macromolecules in said solution by observing how the camphor moves in the solution; inferring and/or confirming a presence of undesirable polymeric macromolecules in the membrane based upon the presence of undesirable polymeric macromolecules in said solution; and purging said membrane of polymeric macromolecules with a surface active molecule.

Samples may be diluted in the sample beaker to obtain quantitative or qualitative determination of higher surfactant concentrations.

The process can be used while continuously filling the sample beaker with a flow stream of the CIP or rinse solution and adding a camphor crystal. Until the camphor crystal starts dancing the flow will be maintained. The dancing determines end of rinse.

The methodologies and the device provided herein cause a reduction in the surface tension of water and can thus be utilized to detect and measure end of rinse for any surfactant active molecule. The surface active molecules could be and are not limited to: most preferred surfactants, soil (membrane foulants, fats, proteins, organics), organic compounds, proteins, molecules as part of cleaners, agents, and food additives.

According to some additional aspects of the present disclosure, the polymeric macromolecules comprise a fatty acid, and the smaller building blocks comprise a fat and an oil.

According to some additional aspects of the present disclosure, the polymeric macromolecules comprise a protein, and the smaller building blocks comprise a peptide and an amino acid.

According to some additional aspects of the present disclosure, the polymeric macromolecules comprise a carbohydrate, and the smaller building blocks comprise a starch and a sugar.

According to some additional aspects of the present disclosure, the polymeric macromolecules comprise a nuclease, and the smaller building blocks comprise a nucleotide.

According to some additional aspects of the present disclosure, the initial cleaning comprises a prerinse step.

According to some additional aspects of the present disclosure, the initial cleaning further comprises a follow-up rinse step.

According to some additional aspects of the present disclosure, the initial cleaning comprises a preclean step.

According to some additional aspects of the present disclosure, the initial cleaning comprises a surface-active molecule with or without the surfactants step.

According to some additional aspects of the present disclosure, the initial cleaning comprises a surfactant step.

According to some additional aspects of the present disclosure, the initial cleaning comprises a plurality of rinse steps.

According to some additional aspects of the present disclosure, the initial cleaning comprises an acid step.

According to some additional aspects of the present disclosure, the initial cleaning comprises an optional alkalinity step.

According to some additional aspects of the present disclosure, the method further comprises utilizing one or more valves to direct and sample the solution in a separate container and waiting until the solution in the separate container is still before applying camphor to said solution.

These and/or other objects, features, advantages, aspects, and/or embodiments will become apparent to those skilled in the art after reviewing the following brief and detailed descriptions of the drawings. The present disclosure encompasses (a) combinations of disclosed aspects and/or embodiments and/or (b) reasonable modifications not shown or described.

BRIEF DESCRIPTION OF THE DRAWINGS

Several embodiments in which the present disclosure can be practiced are illustrated and described in detail, wherein like reference characters represent like components throughout the several views. The drawings are presented for exemplary purposes and may not be to scale unless otherwise indicated.

FIG. 9 tables an exemplary classification system for quantifying movement of camphor crystals in rinse water used in a dairy membrane cleaning application, according to some aspects of the present disclosure.

An artisan of ordinary skill in the art need not view, within isolated figure(s), the near infinite distinct combinations of features described in the following detailed description to facilitate an understanding of the present disclosure.

DETAILED DESCRIPTION

The present disclosure is not to be limited to that described herein. Mechanical, electrical, chemical, procedural, and/or other changes can be made without departing from the spirit and scope of the present disclosure. No features shown or described are essential to permit basic operation of the present disclosure unless otherwise indicated.

Figure 1:
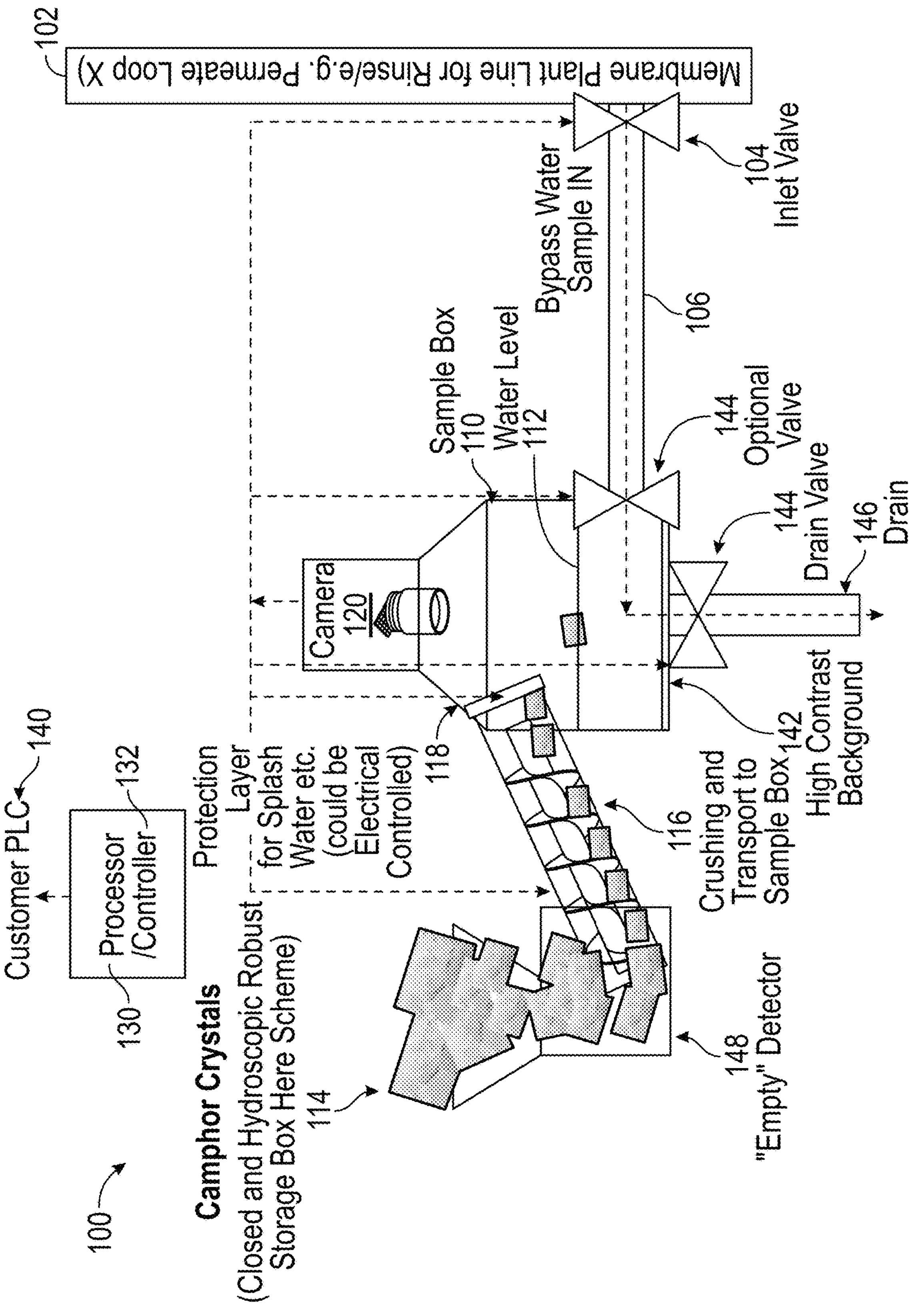
FIG. 1 shows an operative schematic view of a system that includes a camphor-based dynamic tensiometer for detecting the presence of surfactants, according to some aspects of the present disclosure.

Referring now to FIG. 1, a system 100 that includes a camphor-based dynamic tensiometer that utilizes imaging technology for detecting the presence of surfactants. The system includes a membrane plant line 102 for rinse, e.g., permeate loop X. Fluidly downstream therefrom, an inlet valve 104. Opening the inlet valve 104 allows rinse water that has already cleaned said membrane move through piping 106 toward a drain 146 that allows the rinse water to exit after cleaning.

To sample the rinse water for the purpose of detecting surfactants, an optional valve 108 positioned downstream of the inlet valve 104 and located toward an entry point of a sample box 110. The sample box 110 can be a bypass section of the piping 106 and/or a separate container configured to receive at least some of the rinse water. The sample box 110 is preferably open on the top to the environment to allow view of the surface 112 of any fluids therewithin. Camphor crystals 114 can be crushed and transported from a camphor supply by an auger 116 or other suitable actuating mechanism. The camphor crystals can be modulated and released into the sample box 110 so as to contact the surface 112 in order to initiate the process for detecting surfactants in the rinse water. A protective layer 118 for splash water is located at the end of the housing which includes the auger 116. The protective layer 118 can be an elastic flap which is moves out of the way when pressed upon by the camphor crystals 114 or can be a more rigid component that is actuated by an electronic controller (e.g., the central processing unit 130 or the customer programmable logic controller 140).

Camphor Crystals

The camphor crystals 114 comprise camphor, which is a waxy, colorless solid with a strong aroma. Camphor can be characterized by one of the following chemical structures:

Camphor is classified as a terpenoid and a cyclic ketone. Camphor is found in the wood of the camphor laurel (*Cinnamomum camphora*) and in the kapur trec (*Dryobalanops* sp.). Camphor also occurs in some other related trees in the laurel family, notably *Ocotea usambarensis*. Rosemary leaves (*Rosmarinus officinalis*) contain 0.05 to 0.5% camphor, while camphorweed (*Heterotheca*) contains some 5%. A major source of camphor in Asia is camphor basil (the parent of African blue basil). Camphor can also be synthetically produced from oil of turpentine.

Camphor is chiral, existing in two possible enantiomers as shown in the structural diagrams below:

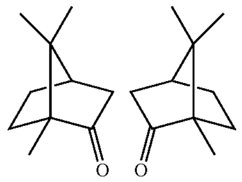

The structure on the left is the naturally occurring (+)-camphor ((1R,4R)-bornan-2-one), while its mirror image shown on the right is the (−)-camphor ((1S,4S)-bornan-2-one). Camphor has few uses in the art and is therefore ripe for a scalable, industrial use due to the ease at which it can be readily purified from natural sources.

In clean rinse water, camphor crystal(s) 114 slowly dissolve at the surface 112 of rinse water within the sample box 110, which lowers the water's surface tension in the immediate neighborhood of the camphor crystal(s) 114. The strange pull exerted by the uncontaminated portion of water brings about a movement of the surface and the camphor particles are carried along with it. This causes the camphor crystal(s) 114 to "dance", suggesting the absence of and/or a minimal amount of surfactants in the fluidic body, above the critical surface tension. In dirtier rinse water, such as that which includes a high load of surfactants, the camphor crystal(s) will not dissolve properly and therefore will not "dance" and/or will only "dance" for a limited amount of time.

Camphor has been produced as a natural, forest product, condensed from the vapor given off by the roasting of wood chips cut from the relevant trees, and later passing steam through the pulverized wood and condensing the vapors. Alternatively, camphor crystals 114 can be synthetically produced from alpha-pinene, which is abundant in the oils of coniferous trees and can be distilled from turpentine produced as a side product of chemical pulping. With acetic acid as the solvent and with catalysis by a strong acid, alpha-pinene intoisobornyl acetate. Hydrolysis of this ester gives isoborneol which can be oxidized to produce racemic camphor.

Alternatives to the camphor crystals 114 that induce motion in fluidic bodies can also be used. Such alternatives could be driven by a difference in surface tension and/or some other suitable mechanism that reacts only when surfactants are present in the fluidic body. The present disclosure contemplates that such alternatives can include but are not limited to including: self-propelled objects coupled with chemical reactions (e.g., a Belousov-Zhabotinsky (BZ) reaction, which is an oscillatory chemical reaction where $Fe(phen)_3^{2+}$ (ferroin), a reduced state of the catalyst, is transformed into $Fe(phen)_3^{3+}$ (ferrin), an oxidation state, and vice versa alternately;), an oxidation state, and vice versa alternately self-propelled droplets (e.g., mercury droplet systems, a butyl salicylate (BS) droplet, etc.).

Camera

Figure 2:
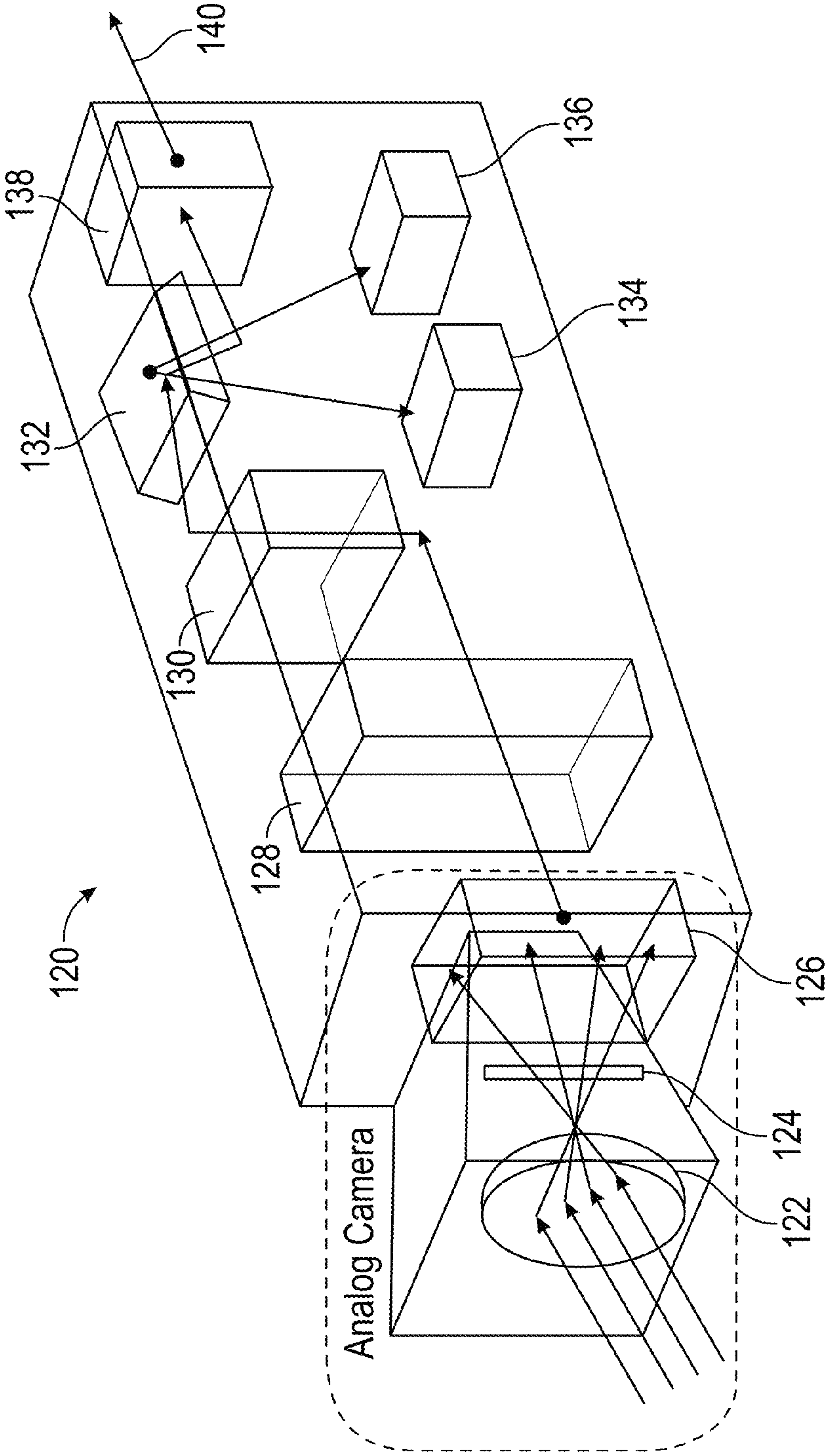
FIG. 2 shows a schematic, perspective view of a video, internet protocol (IP) camera designed to monitor for motion of camphor crystals that can dance at the surface of a fluidic body.

As shown in FIG. 2, a video, internet protocol (IP) camera 120 is provided. The IP camera is a type of digital video camera that receives control data and sends image data via an IP network (e.g., IP network 138). IP cameras can be used for surveillance and monitoring. Unlike analog closed-circuit television (CCTV) cameras, the IP camera 120 does not require a local recording device, instead relying on the local area network. That said, the IP camera 120 can, in some embodiments, be equipped with a local recording device so that the camera can be used in an offline format.

Exemplary components of such a video, IP camera 120 include a camera lens 122 (also known as a photographic lens), shutter 124, optical sensor 126, video audio codec 128, central processing unit 130 (CPU 130), graphics processing unit 132 (GPU 132), flash memory 134, hard disk drive 136, and a network interface 138.

The video, IP camera 120 is specially adapted for detecting movement of camphor crystal(s) 114 at the surface 112 of a fluidic body. The video, IP camera 120 is therefore typically installed in an elevated area, just above the sample box 110, with the camera lens 122 is pointed downward toward the surface of the fluidic medium. There are little differences a lens used for a still camera and the lens 122 used for the video camera 120, and therefore it is to be appreciated that high-speed cameras that take still shots in quick succession can also be used to accomplish similar functionality, e.g., to analyze movement of camphor crystal(s) 114 at the surface 112 of a fluidic body.

While in principle a simple convex lens can suffice, in practice a compound lens made up of a number of optical lens elements is preferred to correct optical aberrations that arise. Some aberrations will be present in any lens system. The lens's design balances the aberrations and produces a design that is suitable for photographic use any particular application, including the application of detection motion of a camphor crystal(s) 114 at the surface 112 of a fluidic body.

The camera lens 122 is used in conjunction with the camera body and an optical mechanism (e.g., shutter 124) to allow light to pass for a determined period, exposing a photosensitive digital sensor 126 or photographic film to light in order to capture a permanent image and/or video recording of a scene.

The video audio codec 128 can take the video or image data file produced by the camera lens 122, the shutter 124, and photosensitive digital sensor 126 and digitally compresses same using a compression algorithm carried out by a central processing unit 130 and a graphics processing unit 132. In some embodiments, the video, IP camera 120 has multiple streaming capabilities, where the video codec will compress each data file input to multiple video files such as H.264, MPEG4, or MJPEG at the same time or multiple image files such as JPEG/JFIF, GIF, BMP, or PNG at the same time. Alternatively, in embodiments where the video, IP camera 120 is an analog camera, the DSP encodes the analog signal to digital signal without compressing the video or image file.

The central processing unit 130 (CPU 130) and the graphics processing unit 132 (GPU 132) of the Video, IP cameras 120 can utilize frame rate control technology. Frame rate control technology sends images at a specified frame rate; thus, only necessary frames are sent. For example, internal programming of a microprocessor in the CPU 130 controls the rate at which photos are taken. In some embodiments, the video, IP camera 120 takes at least ten photos every second and this procedure can be repeated in cycles that last ten seconds.

The central processing unit 130 (CPU 130) and the graphics processing unit 132 (GPU 132) are further responsible for energizing the main circuit, checking circuitry, recording media, and battery status, engaging the camera mode, opening an iris of the lens 122, and adjusting shutter speed of the shutter 124 to get good exposure.

The CPU 130 and the GPU 132 further maintain readiness to take a picture or video by constantly adjusting focus and exposure, stops the gathering of light on the sensor 126, and start reading in values from four to fifty million pixels into frame store.

Pixels have a red, green or blue filter in front of them so as to create a color image. The CPU 130 or the GPU 132 "demosaics" the millions of red, green, and blue dots into a single-color image in mere fractions of a second. The CPU 130 or the GPU 132 does a whole bunch of optimizations (e.g., use of a compression algorithm) to the picture, adjusting brightness, contrast, hue, and saturation of the recorded image and/or video. The CPU/GPU 130, 132 then compresses the image to take up less space, e.g., turned into a JPEG. The CPU/GPU 130, 132 coordinate the sending of the data to the flash memory 134 so that the image can be recorded. The CPU/GPU 130, 132 further prepare and feed the flash memory 134 at a maximum data rate.

The images and/or video recordings of scenes are preferably stored on flash memory 134 because flash memory 134 has a fast read access time, though it is not as fast as static RAM or ROM. Especially where the video, IP camera 120 is a portable device, it is preferred to use flash memory 134 because of their high mechanical shock resistance, as mechanical drives are more prone to mechanical damage.

To avoid the need for an unruly amount of flash memory 134, electronic storage of images can be supplemented with the use of a hard disk drive 136. The hard disk drive 136 stores and retrieves digital data using magnetic storage with one or more rigid rapidly rotating platters coated with magnetic material. The platters can be paired with magnetic heads, usually arranged on a moving actuator arm, which read and write data to the platter surfaces. Data is accessed in a random-access manner, meaning that individual blocks of data can be stored and retrieved in any order. HDDs are another type of non-volatile storage (similar to flash memory 134), retaining stored data when powered off.

Digital videos and images can be streamed through a network 138, processed at an external computer, such as customer programmable logic controller 140, and stored digitally. Video and images can remain digital, and no unnecessary conversions need to be made, thereby resulting in superior image quality. Video, IP cameras 120 connected to networks 138 can therefore provide many beneficial features such as compressing videos and images to minimize video and image streaming over the network 138.

In some embodiments, the IP camera 120 allows for a wired connection to the Internet through the network interface 138. The operable connection to the Internet may be accomplished wirelessly or via an ethernet cable. The IP camera 120 can be connected to either a local area network ("LAN") or a wide area network ("WAN") through a router. Alternatively, the network can also be a neighborhood area network ("NAN"), a home area network ("HAN"), or personal area network ("PAN") employing any of a variety of communications protocols, such as Wi-Fi, Bluetooth, ZigBee, near field communication ("NFC"), etc. Communications through the network by the camera can be protected using one or more encryption techniques, such as those techniques provided in the IEEE 802.1 standard for port-based network security, pre-shared key, Extensible Authentication Protocol ("EAP"), Wired Equivalency Privacy ("WEP"), Temporal Key Integrity Protocol ("TKIP"), Wi-Fi Protected Access ("WPA"), and the like.

The video, IP camera 120 and components thereof may be powered in a number of ways. It is contemplated that the video, IP camera 120 be hard-wired, cord and plug connected, or otherwise powered, such as to AC power plugs and sockets. A hardwired video, IP camera 120 is one where the building wiring method attaches to the camera in a more permanent fashion. This will involve splicing of wires inside the appliance or in a junction box. Cord and plug connected appliances have a cord with a molded plug that is either factory or field installed on the video, IP camera 120. The video, IP camera 120 is then ready to be plugged into a receptacle in the location it is permanently installed. The hard-wired power source could be on a power grid, or could be a separate generator, battery, or other source. The wire could provide Power over Ethernet (PoE) or via USB cable, such as if the system is connected in such a manner. Still further, it is contemplated that the system be self-powered or include on-board power, in that there is no wiring to a separate power source. Such a configuration could include batteries in the video, IP camera 120, such as non-rechargeable (e.g., dry battery) or rechargeable (e.g., Lithium-ion) type batteries. Still further, other types of power, such as, but not limited to, solar, piezoelectric sources, and the like, which can provide additional amounts of power.

Infrared

Figure 3:
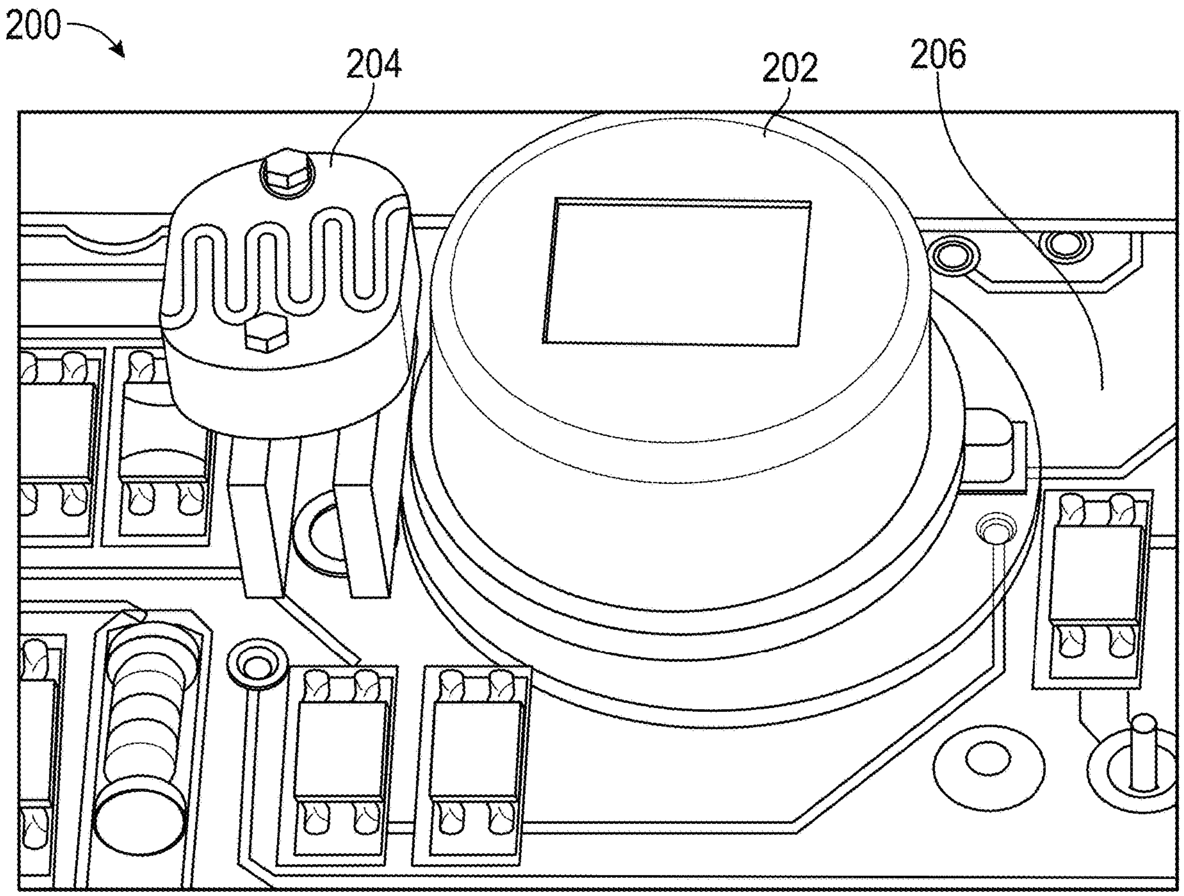
FIG. 3 captures a perspective view of an infrared (IR) module that detect motion and can be included with the IP camera of FIG. 2.
Figure 4:
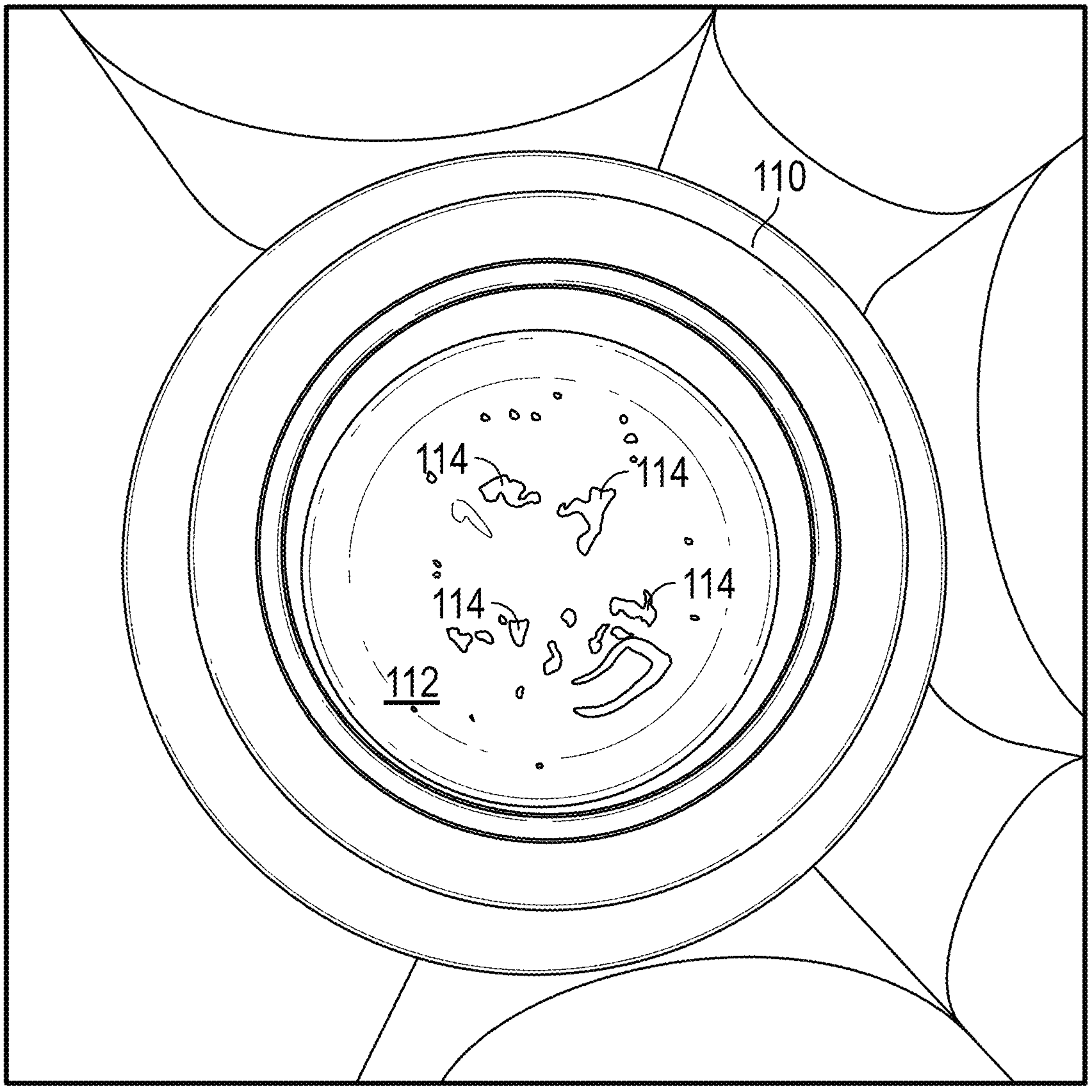
FIG. 4 captures a first still shot of camphor crystals dancing on the surface of rinse water used in a dairy membrane cleaning application, according to some aspects of the present disclosure.
Figure 5:
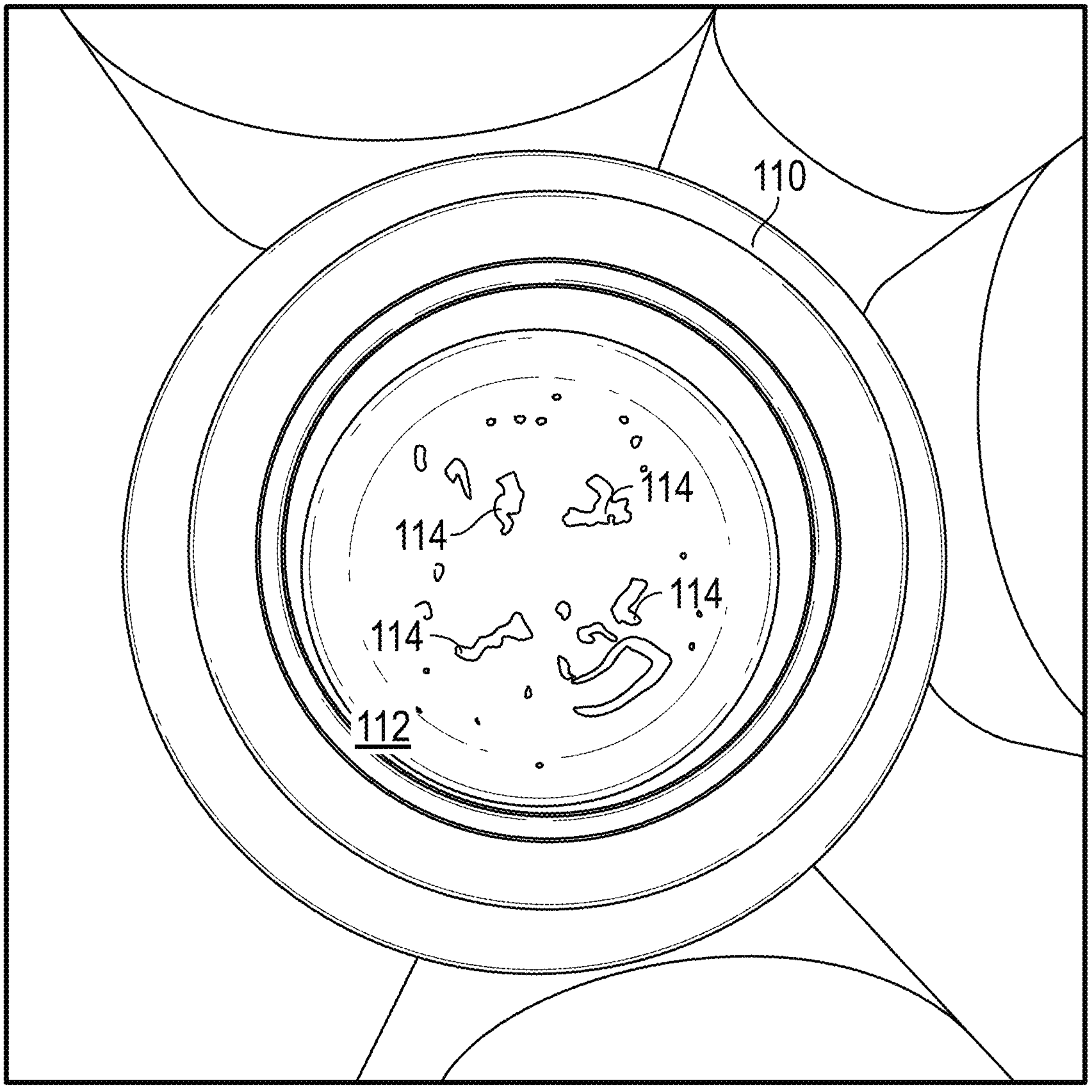
FIG. 5 captures a first still shot of camphor crystals dancing on the surface of rinse water used for a dairy membrane cleaning application, taken after the first still shot of FIG. 4.
Figure 6:
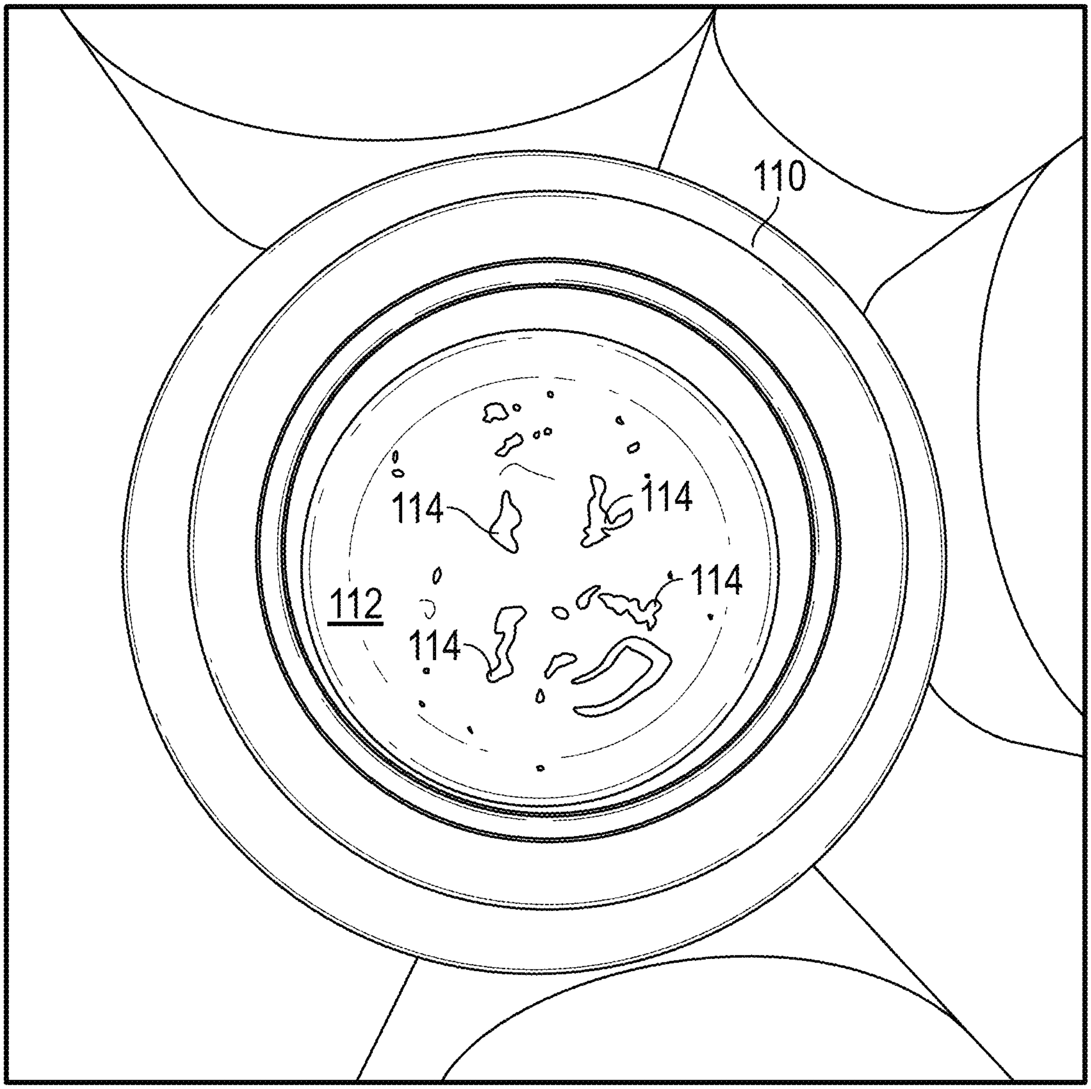
FIG. 6 captures a first still shot of camphor crystals dancing on the surface of rinse water used for a dairy membrane cleaning application, taken after the first still shot of FIGS. 4-5.
Figure 7:
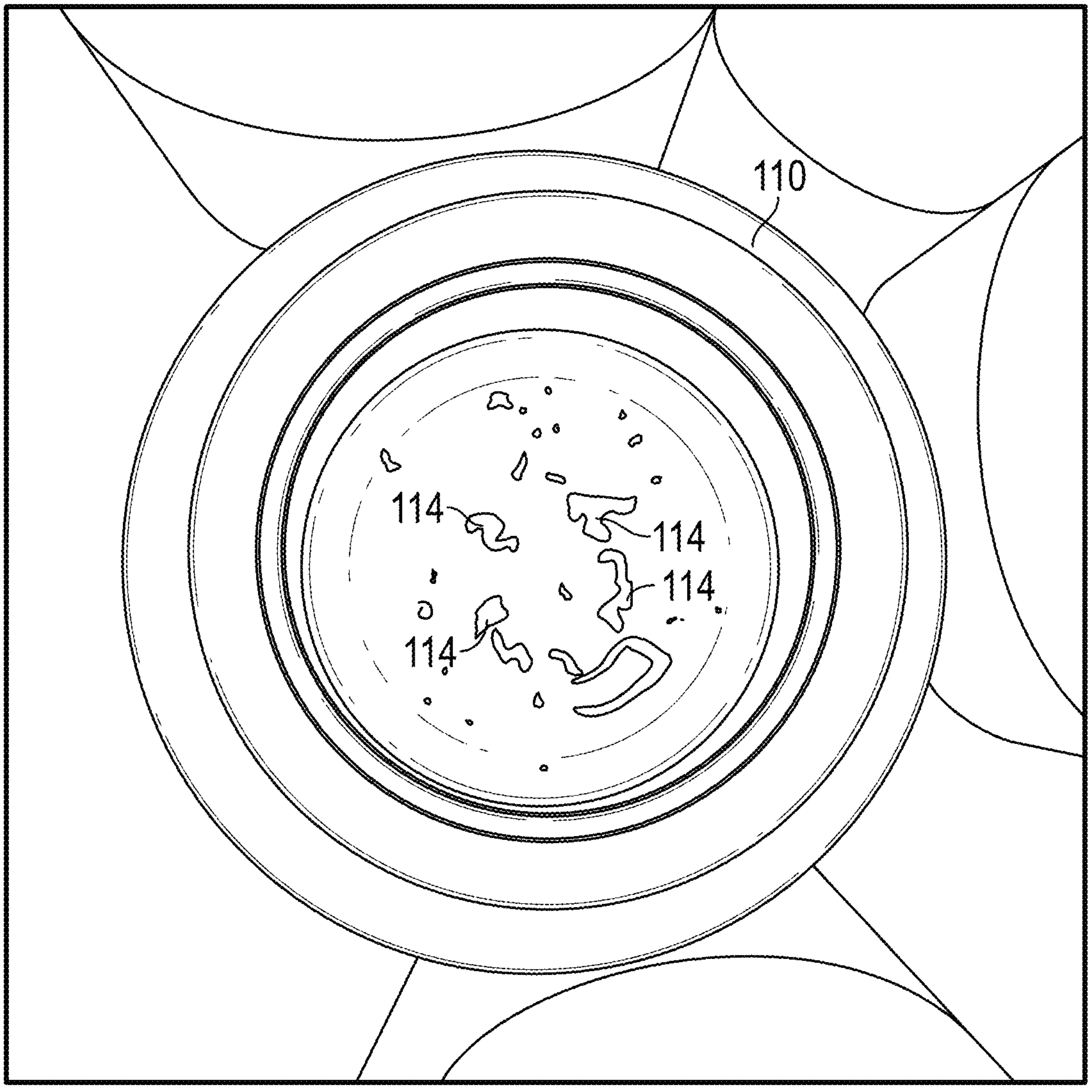
FIG. 7 captures a first still shot of camphor crystals dancing on the surface of rinse water used for a dairy membrane cleaning application, taken after the first still shot of FIGS. 4-6.

In some embodiments, a motion detector with an IR module 200 can be used in addition or can be included within the video, IP camera 120 to quickly identify whether there is any motion in the fluidic body at all. The motion detector is an electrical device that utilizes a sensor to detect nearby motion. The motion can automatically perform a task, such as instructing when the camera should begin recording and/or monitoring for motion of camphor crystal(s) 114 at the surface 112 of a fluidic body or to decrease the time it takes to alert a user there is no motion in the area. FIG. 3 shows an example IR module 200 in greater detail. The IR module 200 can include a passive infrared detector 202 and a photoresistive detector for visible light 204, each mounted on a circuit board 206. This IR module 200, for example, can be used in combination with the high contrast background 142 to instruct the video, IP camera 120 to immediately record and/or monitor for motion of camphor crystal(s) 114 at the surface 112 of a fluidic body when motion is detected.

Figure 8:
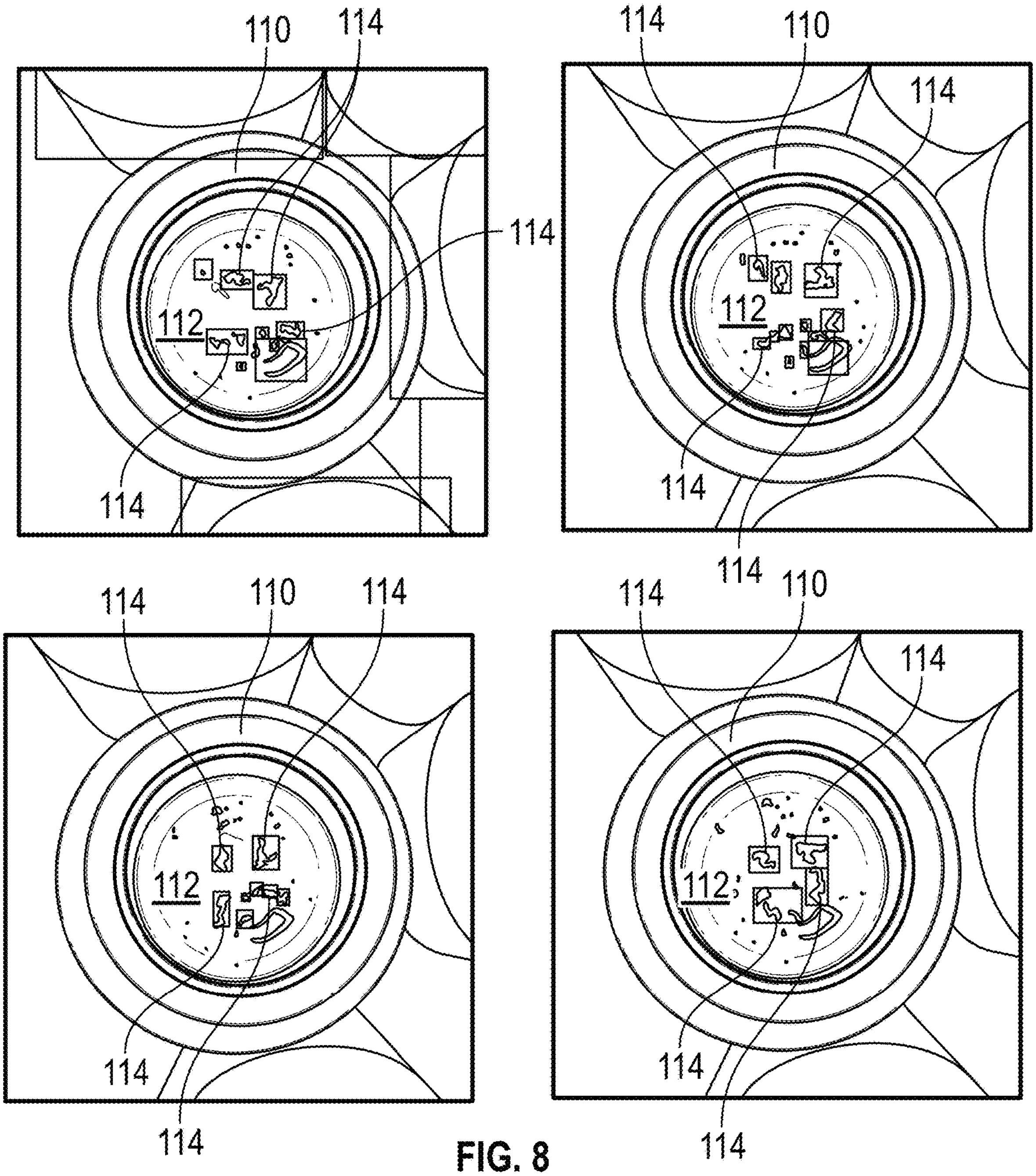
FIG. 8 exemplifies AI-based analysis that interprets potential motion of camphor crystals in rinse water used for a dairy membrane cleaning application, according to some aspects of the present disclosure.

In some embodiments, the video, IP camera 120 can also employ artificial intelligence ("AI") and/or heuristic method(s) to learn how to better identify and improve recognition of movement in a fluidic body that relates to the use of camphor crystal(s) 114 at the surface 112 of a fluidic body, and not movement that is derived from other means. The artificial intelligence model can be based on the concept of a neural network. The purpose of the model is to determine the probability of occurrence of camphor crystal(s) 114 at the surface 112 of a fluidic body on an image (photo), as well as its location. For example, a sequence of four photos (RGB) is captured in FIGS. 4-7. The model then analyses the sequence of photos. The result of the analysis is captured by the still shots of FIG. 8. The photos are made at short intervals and the model generates on the exit a monochromatic (single duct) image with resolution of input photos, where the brightness scale determines whether in a given area there is movement from camphor crystal(s) 114 at the surface 112 of a fluidic body (e.g., a heat map can be created, as spiral thermal waves emerge from the self-propulsion of camphor crystals 114 that float on the surface 112 of water).

The AI utilizes a deep neuron network trained on a great collection of images to recognise their features (recognition of shapes, edges, lines, etc.). Information regarding the movement of the camphor crystal(s) 114 at the surface 112 of a fluidic body, including the location and speed of same, can determine a (i) probability surfactants are present and/or (ii) an amount of surfactants present, in the fluidic body.

Due to the substantial number of layers in the deep neuron network model, training the deepest layers requires a great amount of time and data. Model variables during the training process propagate on a constantly slower rate for subsequent deep network layers. Therefore, already trained models can be used in commercial models.

The network-connected video, IP camera 120 and the artificial intelligence therefore work together and utilize infrared camera technology (see e.g., FIG. 3) to differentiate between camphor-based motion of the camphor crystal(s) 114 at the surface 112 of a fluidic body (which occurs at a first temperature) and any potential surfactants or foreign objects that that only look like the camphor crystal(s) 114 at the surface 112 of a fluidic body (which will generally show up at a second, distinct temperature). The squares in the photos represent potential camphor-related movement. A sequence of photos generally comprises at least three photos, and in FIGS. 4-7 is shown to include four still shots. The photos comprise natural colors, such as colors according to the RGB color model (red, green, blue). Photos in a single sequence represent the same area. While photos can be moved in relation to other photos, only the mutual area common to all of the photos should be analyzed. Delay between making specific photos in a sequence is preferably set to a single increment, such as a tenth of a second (0.1 seconds), though this increment could certainly be sped up or slowed down based on the specific application.

Potential non-movement of certain parts of the photos and/or movement of objects that are not the camphor crystal(s) 114 at the surface 112 of a fluidic body are systematically eliminated as the sequence continues. Elimination is caused by the combination of the algorithm carried out by the central processing unit 130 and/or graphical processing unit 132 and the artificial intelligence in an effort to identify only movement of camphor crystal(s) 114 at the surface 112 of a fluidic body. An infrared (IR) filter may be applied by an IR module 200 to each of the photos in a sequence to help identify movement of camphor crystal(s) 114 at the surface 112 of a fluidic body.

In some embodiments, an operator, via the customer programmable logic controller 140, can manually review the sequence of photos taken by the video, IP camera 120 to begin automatically monitoring for movement of camphor crystal(s) 114 at the surface 112 of a fluidic body, to manually identify motion of camphor crystal(s) 114 at the surface 112 of a fluidic body, and/or to verify results from the AI model to help the AI model better identify movement of camphor crystal(s) 114 at the surface 112 of a fluidic body over time.

The customer programmable logic controller 140 can allow users to give the system with the camphor-based dynamic tensiometer 100 inputs, such as to increase and/or decrease frame rates and/or rates at which photos are taken, to change a weight, volume, and/or an amount of camphor crystal(s) 114 that form the modulated release that gets placed into the sample box 110 each time the camphor-based dynamic tensiometer 100 monitors for motion of camphor crystal(s) 114 at the surface 112 of a fluidic body.

Detection Methods & Classification System

An exemplary method for detecting the presence of a surfactant in rinse water, and therefore a membrane that has been cleaned with the rinse water and the surfactant, comprises water sampling, preparation of a camphor crystal, drop of the camphor crystal in the water, detection of a surface tension, and a rinse.

During water, valves 108 are opened to rinse the sample box 110, the drain valve 144 is closed, the sample box 110 is filled so that the surface 112 is at an adequate level measured via the camera 120, and the inlet valve 104 is closed or is open for a defined time so as to fill to the adequate level. Seconds to relax the system can be critical (i.e., allow for stopping of motion in the water to be sampled) to avoid movement due to water flow, and not the use of the camphor crystal.

During preparation of camphor crystal, camphor crystals 114 are crushed and transported into the sample box 110 by a steel snail, auger 116 or another suitable object. Camphor is a hydroscopic material, therefore the robust crushing into small and adequate pieces and exact dosing (e.g., a modulated release) of a single crystal can, depending on the application, prove to be a key aspect of the design.

During the drop of camphor crystal, the snail/auger 116 and a protection layer 118 are controlled by the controller 140. The layer lid 118 is open and the snail/auger 116 is activated until the time the camera notices a crystal dropping on the water surface 112.

During detection of surface tension, and for a certain time, the camera films the movement of crystal. Either the camera 120 or the controller 140 is programmed to qualitatively cluster the result by analysis. In some embodiments, the analysis is as follows: 0 no movement of crystals 114 (high surfactant load); 1 low movement of crystals 114 with stop after a brief period; 2 medium dancing (after 10 s the crystals 114 stop dancing); and 3 intensive dancing. The total time of the measurement is preferably no more than fifteen seconds, and typically takes between ten and fifteen seconds.

The controller (e.g., CPU 130 and GPU 132) in the camera 120 gives the result to the PLC 140 but also can be connected to stop the rinse if a "0" value is reached.

During rinse, after application of the camphor crystal 114 the sample box 110 is rinsed (optional rinse line controlled). The next sampling water can be used for the rinse to save time.

Finally, it should be appreciated that the speed at which the camphor crystals 114 "dance" can also be quantified. Such speed can be manually observed by a human and/or AI. The manually observed speed can be classified using the subjective classification system 300, which may guide the human to use at least some and/or all of the criteria that is in the center and right-hand columns of FIG. 9, similar to the analysis discussed above. Objective measurements of the rotational speed at which the camphor crystal(s) 114 "dance", e.g., as measured by a motion detector in the video, IP camera 120, can also be taken.

Methods of Initial of Cleaning Membranes: Including Dairy Membranes

Figure 10:
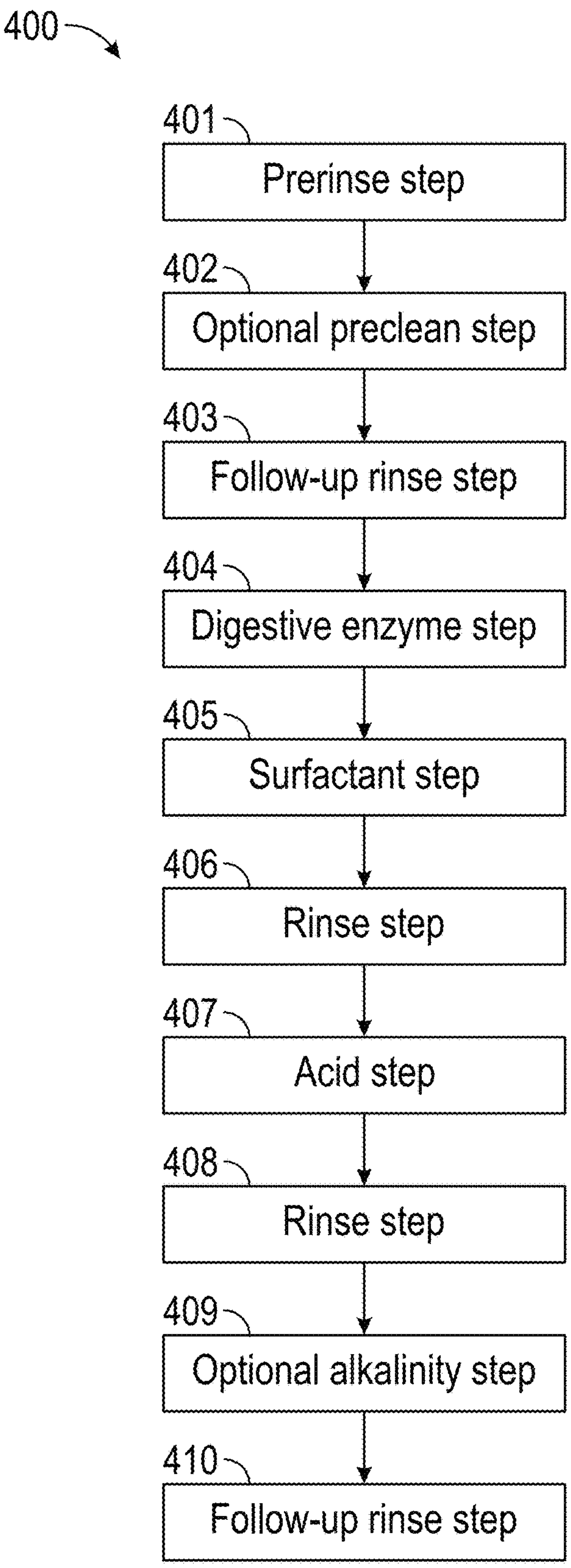
FIG. 10 illustrates a flow diagram of the exemplary method of cleaning dairy membranes.

Disclosed herein are methods 400 of cleaning undesirable polymeric macromolecules. The methods 400 of cleaning can include microfiltration, ultrafiltration, nanofiltration, reverse osmosis, and/or other membrane processes, such as those that are typically utilized in food production. Preferably, the membranes can be cleaned with a stepwise cleaning regime employing a prerinse step 401, an optional preclean step 402, a follow-up rinse step 403, a surface active molecule step 404, a surfactant step 405, a rinse step 406, an acid step 407, a rinse step 408, an optional alkalinity step 409, and a follow-up rinse step 410, as illustrated in FIG. 10 or different combinations of CIP membrane processes.

For example, a method of evaluating cleaning and rinsing of a membrane with a surfactant composition can comprises initially cleaning the membrane with the surfactant composition; monitoring for a presence of an undesirable polymeric macromolecules in a solution that is passed through the membrane after the initial cleaning by applying camphor to said solution; identifying a presence of undesirable polymeric macromolecules in said solution by observing how the camphor moves in the solution; inferring and/or confirming a presence of undesirable polymeric macromolecules in the membrane based upon the presence of undesirable polymeric macromolecules in said solution; and purging said membrane of polymeric macromolecules with a surface active molecule.

Samples may be diluted in the sample beaker to obtain quantitative or qualitative determination of higher surfactant concentrations.

The process can be used while continuously filling the sample beaker with a flow stream of the CIP or rinse solution and adding a camphor crystal. Until the camphor crystal starts dancing the flow will be maintained. The dancing determines end of rinse.

Rinse Step

Upfront the cleaning a rinse is applied to remove foulants from production, also there the device could be used.

Following the surfactant cleaning step, the membrane is rinsed to remove any excess surface-active molecules, surfactant, buffer, and chelant in a rinse step 406. In particular, it is important to remove the any components that can react to form fatty acid salts which cause bad taste to dairy subsequently processed via the dairy filtration membrane. The rinse is preferably performed with water. The water can be tap water or a water that has been softened. The water can have a hardness of about 20 grains or less, preferably about 15 grains or less, more preferably about 10 grains or less, even more preferably 5 grains or less. Most preferably, the water is distilled water or RO (reverse osmosis) water. The rinse water can be any temperature for which the membrane is compatible. Thus, tap water can be used, room temperature water can used, or heated water can be used so long as it does not exceed the temperature guidelines for the particular membrane. For most membranes, this will be up to 50° C. For high temperature membranes, this can be up to 60° C. or even up to 70° C. For a standard membrane, preferably the temperature of the rinse water is between 20° C. and 50° C., more preferably between 25° C. and 50° C., most preferably between 30° C. and 50° C. for a high temperature membrane, preferably the temperature of the rinse water is between 20° C. and 70° C., more preferably between 25° C. and 70° C., most preferably between 30° C. and 70° C.

Other Modifications to the Method(s) Described Herein

Any cleaning steps can be used together with the invention in the event rotational and/or oscillatory movement of camphor crystals 114 is not detected and/or is slow at the surface 112 of the fluidic body, as this suggests the presence of surfactants and/or other polymeric macromolecules that are harmful for human consumption. For example, the controller can instruct another surface active molecule to be used in addition to rinse water at the membrane so as to further purge the membrane of said surfactants and/or other polymeric macromolecules that are harmful for human consumption.

Non-limitingly, CIP methods 400 can also employ turbulent flow through piping, or spray balls for large surfaces. In some cases, CIP cleaning methods 400 can also be accomplished with fill, soak, and agitate.

From the foregoing, it can be seen that the present disclosure accomplishes at least all of the stated objectives.

LIST OF REFERENCE CHARACTERS

The following table of reference characters and descriptors are not exhaustive, nor limiting, and include reasonable equivalents. If possible, elements identified by a reference character below and/or those elements which are near ubiquitous within the art can replace or supplement any element identified by another reference character.

TABLE 1

| List of Reference Characters | |
|---|---|
| 100 | system that includes a camphor-based dynamic tensiometer for detecting the presence of surfactants |
| 102 | membrane plant line for rinse, e.g., permeate loop X |
| 104 | inlet valve |
| 106 | piping |
| 108 | optional valve |
| 110 | sample box |
| 112 | surface of fluidic body |
| 114 | camphor crystal(s) |
| 116 | auger for crushing and transport of camphor crystal(s) to sample box |
| 118 | protective layer |
| 120 | camera (e.g., video camera, internet protocol camera, video IP camera, IR camera, etc.) |
| 122 | camera lens |
| 124 | shutter |
| 126 | optical sensor |
| 128 | video audio codec |
| 130 | central processing unit (CPU) |
| 132 | graphics processing unit (GPU) |
| 134 | flash memory |
| 136 | hard disk drive |
| 138 | network interface |
| 140 | customer programmable logic controller |
| 142 | high contrast background |
| 144 | drain valve |
| 146 | drain |
| 148 | load sensor |
| 200 | IR module |
| 202 | passive infrared detector |
| 204 | photoresistive detector for visible light |
| 206 | circuit board |
| 300 | exemplary classification system |
| 400 | method for cleaning a solution comprising undesirable polymeric macromolecules |
| 401 | prerinse step |
| 402 | optional preclean step |
| 403 | follow-up rinse step |
| 404 | surface active molecule step |
| 405 | surfactant step |
| 406 | rinse step |
| 407 | acid step |
| 408 | rinse step |
| 409 | optional alkalinity step |
| 410 | follow-up rinse step |

GLOSSARY

Unless defined otherwise, all technical and scientific terms used above have the same meaning as commonly understood by one of ordinary skill in the art to which embodiments of the present disclosure pertain.

The terms "a," "an," and "the" include both singular and plural referents.

The term "or" is synonymous with "and/or" and means any one member or combination of members of a particular list.

As used herein, the term "exemplary" refers to an example, an instance, or an illustration, and does not indicate a most preferred embodiment unless otherwise stated.

The term "about" as used herein refers to slight variations in numerical quantities with respect to any quantifiable variable. Inadvertent error can occur, for example, through use of typical measuring techniques or equipment or from differences in the manufacture, source, or purity of components.

The term "substantially" refers to a great or significant extent. "Substantially" can thus refer to a plurality, majority, and/or a supermajority of said quantifiable variables, given proper context.

The term "generally" encompasses both "about" and "substantially."

The term "configured" describes structure capable of performing a task or adopting a particular configuration. The term "configured" can be used interchangeably with other similar phrases, such as constructed, arranged, adapted, manufactured, and the like.

Terms characterizing sequential order, a position, and/or an orientation are not limiting and are only referenced according to the views presented.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾. This applies regardless of the breadth of the range.

The methods and compositions of the present invention may comprise, consist essentially of, or consist of the components and ingredients of the present invention as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

The term "actives" or "percent actives" or "percent by weight actives" or "actives concentration" are used interchangeably herein and refers to the concentration of those ingredients involved in cleaning expressed as a percentage minus inert ingredients such as water or salts. It is also sometimes indicated by a percentage in parentheses, for example, "chemical (10%)."

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

"Clean-in-place" (CIP) is a method of automated cleaning the interior surfaces of pipes, vessels, equipment, filters and associated fittings, without major disassembly. CIP is commonly used for equipment such as piping, tanks, and fillers.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, auto dish sanitizers, sanitizing gels, cooling towers, food processing antimicrobial garment sprays, and non-to-low-aqueous food preparation lubricants, oils, and rinse additives.

The term "hard surface" refers to a solid, substantially non-flexible surface such as a countertop, tile, floor, wall, panel, window, plumbing fixture, kitchen and bathroom furniture, appliance, engine, circuit board, dish, mirror, window, monitor, touch screen, and thermostat. Hard surfaces are not limited by the material; for example, a hard surface can be glass, metal, tile, vinyl, linoleum, composite, wood, plastic, etc. Hard surfaces may include for example, health care surfaces and food processing surfaces.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the term "substantially free" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%.

The terms "water soluble" and "water dispersible" as used herein, means that the ingredient is soluble or dispersible in water in the inventive compositions. In general, the ingredient should be soluble or dispersible at 25° C. concentration of between about 0.1 wt. % and about 15 wt. % of the water, more preferably at a concentration of between about 0.1 wt. % and about 10 wt. %.

The term "weight percent," "wt. %," "wt-%," "percent by weight," "% by weight," and variations thereof, as used herein, refer to the concentration of a substance as the weight of that substance divided by the total weight of the composition and multiplied by 100.

The "invention" is not intended to refer to any single embodiment of the particular invention but encompass all possible embodiments as described in the specification and the claims. The "scope" of the present disclosure is defined by the appended claims, along with the full scope of equivalents to which such claims are entitled. The scope of the disclosure is further qualified as including any possible modification to any of the aspects and/or embodiments disclosed herein which would result in other embodiments, combinations, subcombinations, or the like that would be obvious to those skilled in the art.

What is claimed is:

1. A process for evaluating characteristics of a fluidic body comprising:

sampling a portion of the fluidic body;

applying camphor crystals to the sampled portion of the fluidic body;

monitoring movement of the camphor crystals in the sampled portion of the fluidic body with imaging technology;

determining whether the camphor crystals are dancing in the sampled portion of the fluidic body; and quantifying an amount of surfactants in a rinse water based upon the determination of whether the camphor crystals are dancing in the sampled portion of the fluidic body.

2. The process of claim 1 wherein the determination of whether the camphor crystals are dancing in the sampled portion of the fluidic body further comprises determining a degree to which the camphor crystals are dancing in the sampled portion of the fluidic body.

3. The process of claim 1 wherein the sampled portion of the fluidic body is sampled within a bypass section of piping or within a sample box.

4. The process of claim 3 wherein the application of camphor crystals to a sampled rinse water occurs in a modulated release.

5. The process of claim 4 wherein a weight, volume, and/or amount of the camphor crystals released in the modulated release is automatically determined by a controller.

6. The process of claim 5 further comprising crushing and transporting the camphor crystals to the bypass section of piping or to the sample box.

7. The process of claim 6 wherein a load sensor alerts a user when an amount of the camphor crystals in the camphor supply is low.

8. The process of claim 1 further comprising analyzing whether there is a presence of surfactants in the sampled fluidic body.

9. The process of claim 8 wherein the fluidic body is rinse water that has been used to clean dairy membranes.

10. The process of claim 8 wherein the analyzing comprises evaluating a sequence of images captured in succession at a set time interval.

11. The process of claim 10 wherein the analyzing is carried out by artificial intelligence (AI), by the imaging technology, and/or a customer programmable logic controller.

12. The process of claim 11 further comprising compressing the sequence of images.

13. The process of claim 1 wherein the imaging technology comprises a video camera or an IR module for detecting motion of objects in the sampled portion of the fluidic body with imaging technology.

14. The process of claim 1 further comprising utilizing a high contrast background to facilitate the determination of whether the camphor crystals are dancing in the sampled portion of the fluidic body.

15. A process for evaluating characteristics of a fluidic body comprising:

transporting a mechanism from a supply to a surface of the fluidic body;

activating the mechanism by utilizing a difference in surface tension in a first area of a fluidic body and a second area of the fluidic body proximate the first area;

monitoring rotational and/or oscillatory movement of the mechanism with imaging technology; and classifying and/or quantifying the rotational and/or oscillatory movement of the mechanism with imaging technology and a controller; and wherein the mechanism comprises an oscillatory chemical reaction comprising Fe(phen)32+ (ferroin) transforming into Fe(phen)33+ (ferrin) alternately.

* * * * *